(12) United States Patent
Furusawa (10) Patent No.: US 7,760,361 B2
(45) Date of Patent: Jul. 20, 2010

(54) SURFACE PLASMON DETECTION USING CURVED SURFACE PRISM AND REFLECTING MEMBER

(75) Inventor: Kentaro Furusawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 225 days.

(21) Appl. No.: 12/169,354

(22) Filed: Jul. 8, 2008

(65) Prior Publication Data

US 2009/0027680 A1 Jan. 29, 2009

(30) Foreign Application Priority Data

Jul. 10, 2007 (JP) ............................. 2007-180899

(51) Int. Cl.
*G01N 21/55* (2006.01)
(52) U.S. Cl. ..................................................... 356/445
(58) Field of Classification Search ................. 356/445; 422/55
See application file for complete search history.

(56) References Cited

U.S. PATENT DOCUMENTS

2002/0009812 A1* 1/2002 Miura et al. ................. 436/518
2006/0114756 A1* 6/2006 Kojima et al. ............ 369/13.17

* cited by examiner

*Primary Examiner*—Roy Punnoose
(74) *Attorney, Agent, or Firm*—Fitzpatrick, Cella, Harper & Scinto

(57) ABSTRACT

A detection apparatus arranges a light source, a curved surface prism having a curved surface and a plane surface, a metal film placed on the plane surface of the prism to be held adjacently to a test sample, and a reflecting member for reflecting light such that light emitted by the light source enters the prism through the curved surface and is reflected by the metal film, then by the reflecting member, and again by the metal film. The detection apparatus is adapted to detect an optical change in the test sample by means of surface plasmon generated on the metal film. In the detection apparatus, divergent light is made to enter the prism through the curved surface to collimate the incident light by means of the curved surface. The apparatus can suppress the broadening of the resonant bandwidth so as to operate as a monitor with a higher degree of precision.

16 Claims, 6 Drawing Sheets

SURFACE PLASMON DETECTION USING CURVED SURFACE PRISM AND REFLECTING MEMBER

BACKGROUND OF THE INVENTION

1. Field of the Invention

This invention relates to a detection apparatus utilizing plasmon resonance so as to be operated for monitoring a change in the surface condition in terms of refractive index, temperature and so on particularly due to a reaction and also to a method of detecting an optical change in a test sample.

2. Description of the Related Art

Sensors utilizing plasmon resonance actually utilize surface plasmon resonance (SPR) that exists on the interface of metal and dielectric. Plasmons on a plane interface have an electric field distribution in a space of not more than several hundred nanometers near the surface and hence such sensors have applications as refractive index sensors that are highly sensitive in the vicinity of a surface.

With plasmon resonance, the resonant angle and the resonant wavelength shift as the surface condition changes. Particularly, in the case of an SPR sensor, the dependency of the reflectance on the angle of incidence or the change in the reflectance as a function of the angle of incidence is detected as the response of the sensor, using a total reflection configuration (which is generally referred to as Kretschmann configuration) by way of a prism. Such an apparatus is referred to as ATR (attenuated total reflection) apparatus. An apparatus having a simple configuration as illustrated in Review of Scientific Instruments, Vol. 60, p. 1201 (1989) has been proposed (see FIG. 8 of the accompanying drawings).

Figure 8:
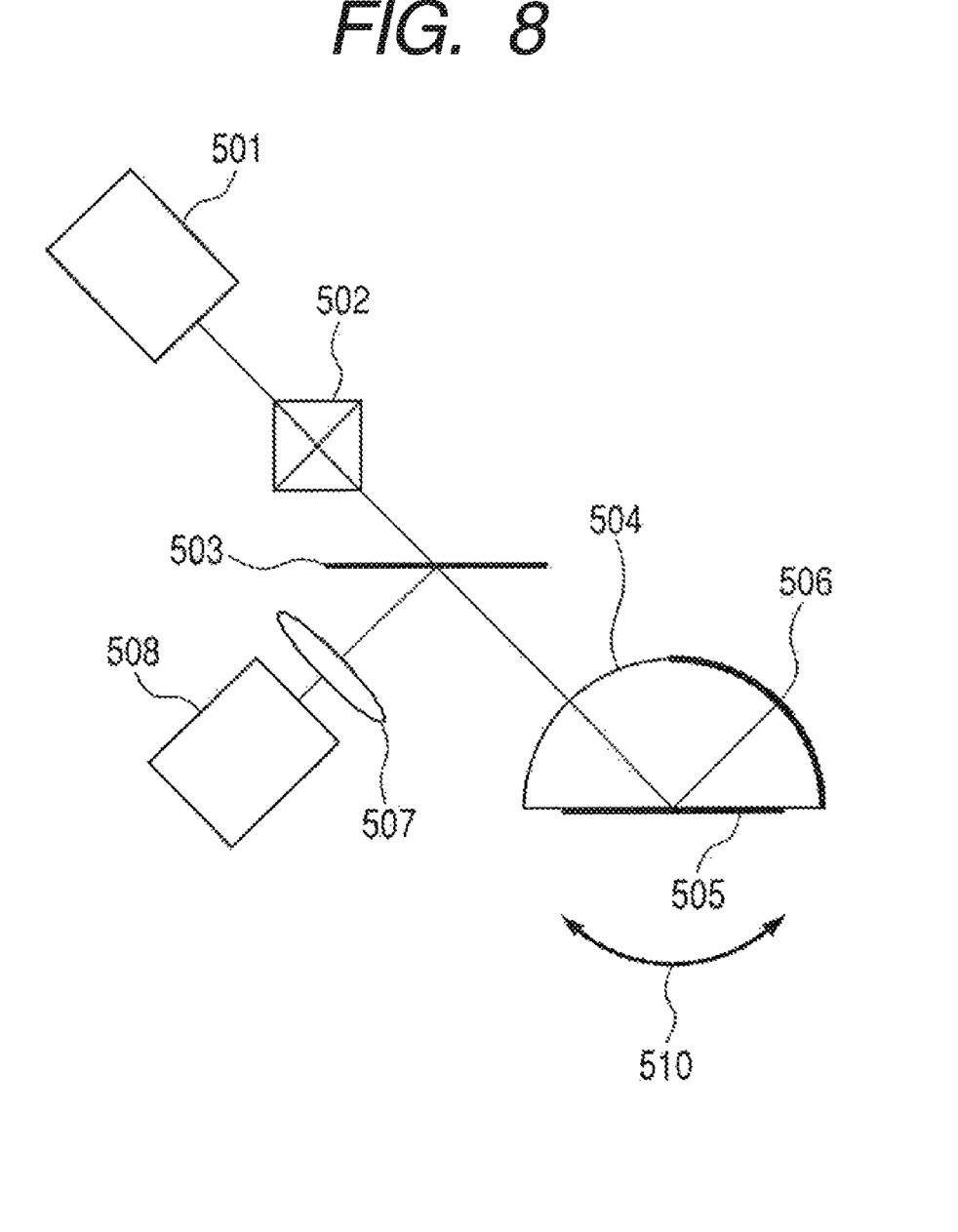
FIG. 8 is a schematic illustration of a known detection apparatus.

With an apparatus illustrated in FIG. 8, light emitted from a light source 501 is adjusted for polarization by way of a polarizer 502 and then transmitted through a beam splitter 503. The light is then made to enter a hemispherical prism 504 having a metal thin film 505 arranged on the plane thereof and reflected by the interface of the metal thin film 505 and the hemispherical prism 504.

A sample, or an object of observation, is arranged on the metal thin film 505 and the intensity of reflected light changes due to plasmon interaction at the interface of the metal thin film 505 and the sample.

The reflected light squarely strikes the reflecting film 506 that is formed by coating on part of the curved surface of the hemispherical prism 504 and reflected by the film 506 and then again by the planar interface of the hemispherical prism 504 and the metal thin film 505. Ultimately, the light reflected by the beam splitter 503 is converged to a detector 508 by means of a lens 507. Generally, such an apparatus is referred to as SPR sensor of double path configuration.

With a popular SPR sensor of Kretschmann configuration using a triangular prism, at least two out of three components including a light source component, a prism component and a detection component are driven to move relative to each other for angle scanning.

However, with an SPR sensor of double path configuration as illustrated in FIG. 8, a rotary mechanism 510 for driving a hemispherical prism 504 around the reflecting point thereof to rotate is employed for angle scanning.

In other words, the sensor can be made structurally simple since angle scanning can be realized by driving only a prism component (hemispherical prism 504).

An ATR apparatus of double path configuration illustrated in FIG. 8 provides advantages including that it is compact, that the number of parts that are driven to move is small and that a high degree of signal modulation (square) can be achieved if compared with conventional apparatus of single path configuration.

However, an apparatus as illustrated in FIG. 8 is accompanied by a problem that the plasmon resonance spectrum is apt to be broadened due to the spherical aberration that takes place when light enters the hemispherical prism 504 and the fact that the radius of curvature of the beam wavefront tends to become small.

Therefore, the object of the present invention is to provide an ATR apparatus (plasmon sensor) of double path configuration that can suppress the broadening of the resonant bandwidth so as to operate as a monitor with a higher degree of precision.

SUMMARY OF THE INVENTION

A detection apparatus according to the present invention includes a light source for emitting light, a curved surface prism having a curved surface and a plane surface, a metal film placed on the plane surface to be held adjacently to a test sample, and a reflecting member for reflecting light, wherein the light source, the curved surface prism, the metal film and the reflecting member are arranged such that light emitted by the light source enters the prism through the curved surface and is reflected by the metal film, then by the reflecting member, and again by the metal film, wherein the apparatus is adapted to detect an optical change in the test sample by means of surface plasmon generated on the metal film, and wherein divergent light is made to enter the curved surface of the prism to collimate the incident light by means of the curved surface.

A method according to the present invention for detecting an optical change in a test sample by means of surface plasmon generated on a metal film includes: arranging a light source for emitting light, a curved surface prism having a curved surface and a plane surface, a metal film placed on the plane surface of the prism, and a reflecting member for reflecting light such that light emitted by the light source enters the prism through the curved surface and is reflected by the metal film, then by the reflecting member, and again by the metal film; bringing the test sample into contact with the metal film; having the light source emit light and making the light enter the prism through the curved surface as divergent light; and making the light reflected by the metal film, by the reflecting member and again by the metal film to enter a detector to detect a change in resonance condition of surface plasmon generated on the metal film in response to an optical change in the test sample.

An apparatus according to the present invention is designed to make divergent light enter the curved surface of a curved surface prism and collimate the incident divergent light by means of the curved surface prism. Then, as a result, the light entering the curved surface prism by way of the curved surface thereof is collimated before it strikes the metal film arranged on the plane surface of the curved surface prism. The light reflected by the metal film, then passing through the curved surface of the curved surface prism and reflected by the reflecting member is collimated once again by the curved surface prism before it strikes the metal film. As a result, the light that strikes the metal film twice is always collimated with a neatly arranged wavefront so that the radius of curvature of the wavefront of the light beam is reduced when striking the metal film. Thus, the bandwidth of the resonance peak of the plasmon resonance generated on the metal film can be narrowed and hence the optical change in the test sample can be detected with a high degree of precision.

Further features of the present invention will become apparent from the following description of exemplary embodiments with reference to the attached drawings.

DESCRIPTION OF THE EMBODIMENTS

Now, the present invention will be described in greater detail by referring to the accompanying drawings that illustrate preferred embodiments of the invention.

With the detection apparatus of this embodiment, the plane surface of the curved surface prism is brought into contact with the metal film and then the metal film is brought into contact with a test sample. Light is made to strike the metal film and light reflected by the metal film is detected.

When a change takes place in the test sample, the condition on which surface plasmon is generated at the metal film changes.

Therefore, the quantity of detected light indicates a change. Thus, the optical change in the test sample can be monitored by monitoring the change in the quantity of detected light. The metal film may be arranged on the curved surface prism of the detection apparatus or, alternatively, at the side of the element equipped with the test sample.

The change in the optical signal detected by means of this embodiment may typically be a change in the resonance peak position (angle) that takes place before and after the reaction of an antigen contained in the test sample and an antibody that specifically reacts with the antigen when the antigen is previously anchored rigidly to the surface of the metal film in order to detect the antigen.

The change in the optical signal may alternatively be detected as the change in the resonance condition attributable to any of various possible changes in the dielectric constant of the surface of the metal film. However, the change in the optical signal will be described below in terms of a signal of ATR (attenuated total reflection), which is most popular.

Figure 1:
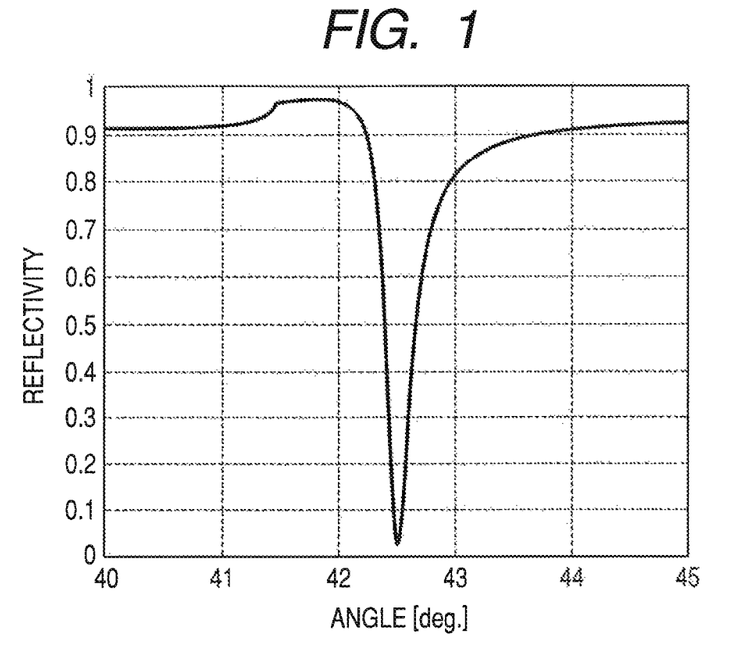
FIG. 1 is a graph illustrating theoretical SPR signal R' (θ).

An ATR spectrum can be theoretically expressed by considering Fresnel reflection. FIG. 1 is an example of computation of ATR for a system having a 50 nm-thick thin film of Au (gold) on a BK7 substrate. The ATR is detected by observing the change in the reflectance ΔR in an actual measurement, which can be expressed by formula (1) illustrated below:

$$\Delta R = \frac{\partial R}{\partial \theta}\bigg|_{\theta=\theta_{1/2}} \frac{\partial \theta}{\partial s}\Delta s \tag{1}$$

where Δs is the mass of the object of detection.

In the above formula, the first term indicates the gradient of the angular spectrum whereas the second term indicates the quantity of the shift relative to the perturbation. From the formula (1), it will be seen that a maximum sensitivity can be achieved by observing the quantity of the change in the beam intensity at the angle that gives the largest gradient of the angular spectrum.

Therefore, obtaining a large gradient value is an important factor for the purpose of improving the sensitivity.

However, the angular spectrum of an incident beam is superimposed in an actual system. If the angle-dependency of ATR is R'(θ) and the angular spectrum of the incident beam of light is S(θ), the ATR spectrum that is actually observed is expressed by formula (2) below.

$$R(\theta)=\int_{-\infty}^{\infty}R'(0-\theta')S(\theta')d\theta' \tag{2}$$

Differently stated, if the observer believes that he or she is observing the reflectance at a certain angle of incidence, what is detected is a signal representing the total sum of the contributions of the components included in the angular spectrum of the incident beam of light.

Figure 2:
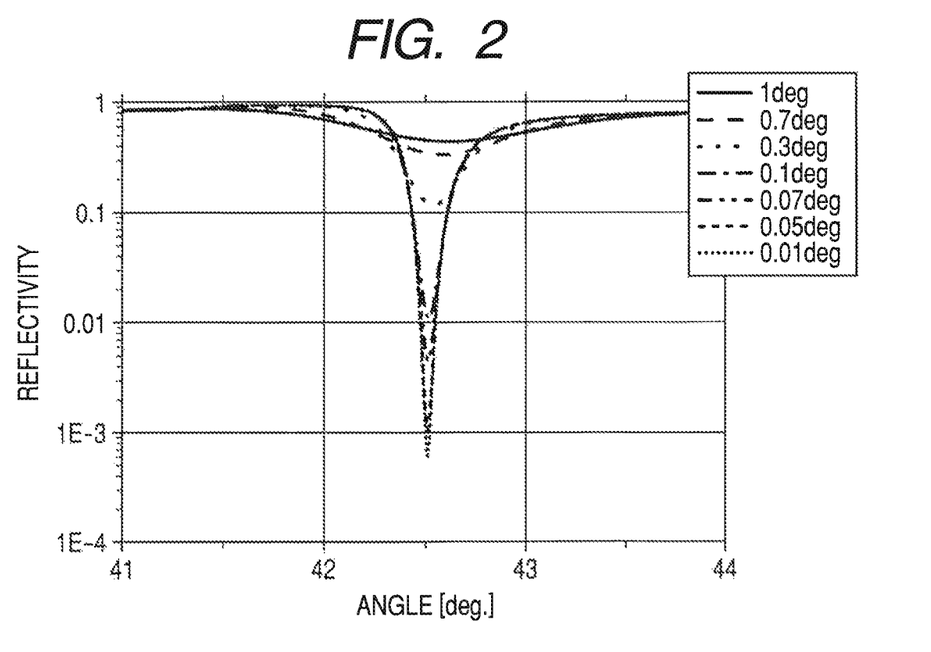
FIG. 2 is a graph illustrating an ATR signal that can be obtained when the angular spectrum of a beam of light shows various widths.

FIG. 2 illustrates how R(θ) changes when S(θ) having various half bandwidths is introduced for R'(θ). It will be seen that the peak width is increased in R(θ) that provides the ATR signal when the spreading angle S(θ) of the beam of light is large.

In the instance of FIG. 2, the peak in R(θ) does not illustrate any substantial broadening and hence the measured value is not practically degraded when the width of S(θ) is about 0.1°. Ideally, the half bandwidth of S(θ) and hence that of the angular spectrum of incident light at the position of the focal point on the metal film is not greater than 1/10 of the half bandwidth of R(θ) and therefore that of the resonance spectrum. Preferably such a value is realized both on the way moving forward from the light source side to the metal film and on the way moving backward from the reflecting mirror side to the metal film.

Figure 3:
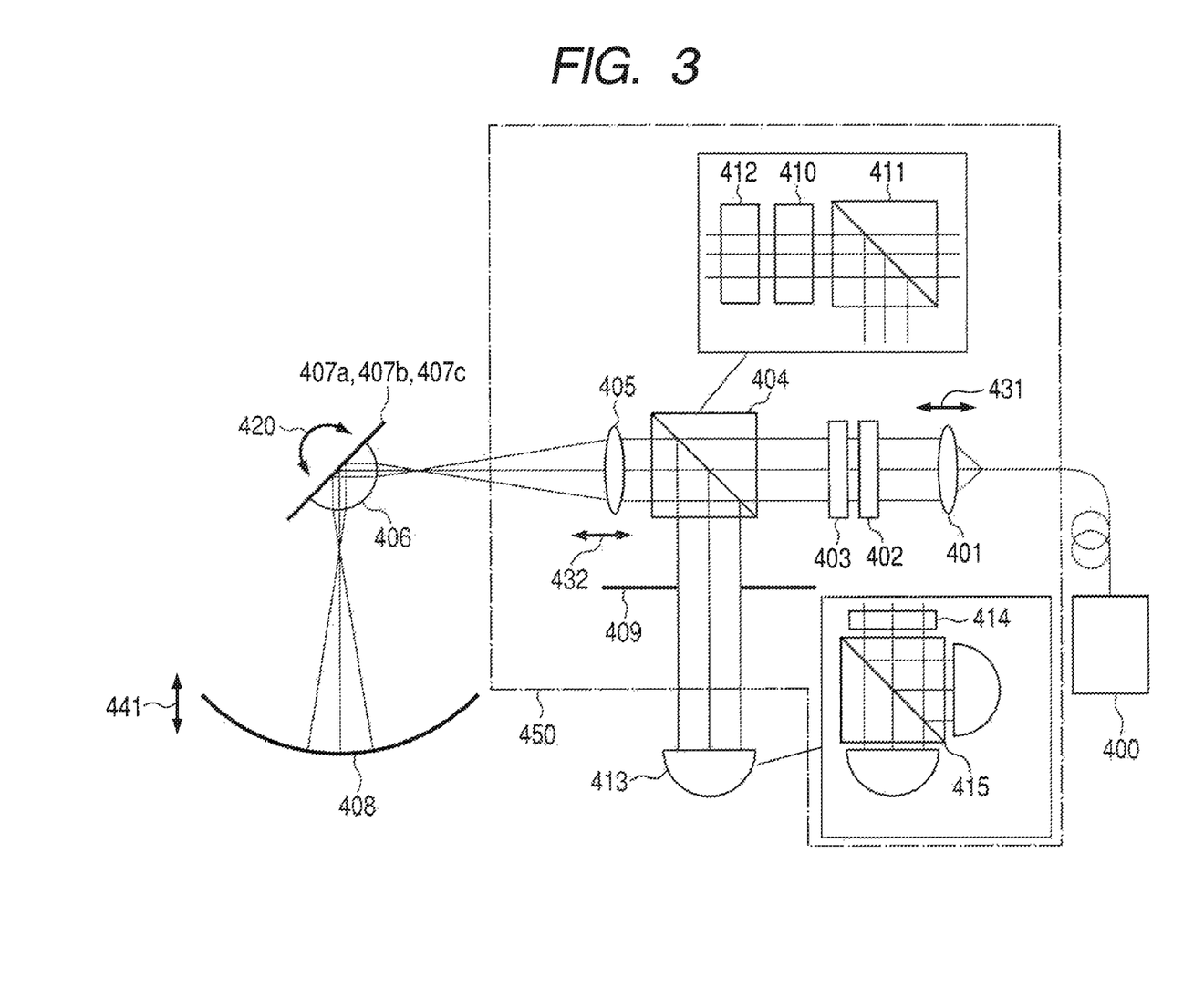
FIG. 3 is a schematic illustration of a configuration of an embodiment of detection apparatus according to the present invention.

The apparatus illustrated in FIG. 3 is a typical embodiment of the present invention. This embodiment is realized by considering an arrangement by means of which both the light of beam moving forward and the light of beam moving backward in the curved surface prism are collimated. In other words, divergent light is made to enter the curved surface prism from the curved surface thereof and collimated in the prism so that the collimated light is propagated in the prism both on the way where light moves forward and on the way where light moves backward.

In the apparatus of FIG. 3, a hemispherical prism 406 operates as curved surface prism and a divergent light generating unit 450 causes divergent light to enter the curved surface prism from the curved surface thereof. The unit 450 may have a configuration selected from a variety of possible configurations for causing the divergent light to enter the curved surface prism. Reference numeral 400 denotes a light source. A reflecting member 408 is so arranged as to be separated from the curved surface prism 406. It is provided to cause the divergent light to enter the curved surface prism 406 and become collimated before striking a metal film 407a. Then, it returns the light reflected by the metal film back to the metal film 407a once again. With the illustrated apparatus, the divergent light is made to enter the curved surface prism 406 and collimated in the curved surface prism on the way moving forward. Then, the light is made to strike the reflecting member 408 as divergent light and enter the curved surface prism once again as divergent light after being reflected by the reflecting member 408. Thus, the light is collimated both on the way where light moves forward and on the way where light moves backward in the curved surface prism.

In the present invention, collimating of the light does not merely mean perfect collimation of divergent light but a bit of collimation of the light.

With the detection apparatus illustrated in FIG. 3, light emitted from the light emitting end of the fiber of the light source 400 enters the divergent light generating unit 450 as unipolarized wave. The unipolarized wave is then collimated as the unipolarized wave is made to pass through a collimator lens 401. Thereafter, the wave is made to pass through a modulator 402 and a half-wave plate 403 so as to illustrate a desired state of polarization. Then, the collimated beam of light is converged by a converging lens 405 and made to enter the hemispherical prism 406 by way of a beam splitter 404. A beam expander and/or a beam diameter adjustment mechanism may be arranged at desired positions for the collimated beam of light. A metal film 407a is arranged on the planar part of hemispherical prism 406 and a test sample 407c is held at a position adjacent to the metal film 407a by means of a sample holding mechanism 407b. The sample holding mechanism 407b may be adapted to hold not only the test sample 407c but also the metal film 407a that is put together with the test sample 407c.

The converged beam of light is focused immediately before the hemispherical prism 406 and collimated in the hemispherical prism 406 before it is irradiated onto the metal film 407a (in a substantially collimated condition).

The beam of light that is reflected by the metal film 407a is converted once again outside the hemispherical prism 406 and thereafter made to become divergent before it squarely strikes the concave mirror (reflecting mirror) 408, which is a reflecting member, and is reflected by the latter to strike the metal film 407a once again. The radius of curvature of the concave mirror 408 is substantially equal to the optical distance between the point of re-convergence and the concave mirror 408.

The (returning) beam of light is reflected by the surface of the test sample 407c as a substantially collimated flux of light like the entering beam of light and, after passing through the converging lens 405, reflected by the beam splitter 404 before entering the detector 413.

In the detection apparatus of this embodiment, a rotary mechanism 420 for driving the beam of light to rotate around the focal point of the beam is annexed to the hemispherical prism 406 as schematically indicated by a double arrow in FIG. 3. The angle of incidence of the beam of light can be shifted by means of the rotary mechanism 420 for observation and hence for angle scanning.

The collimator lens 401 and the converging lens 405 are equipped with respective position adjustment mechanisms 431, 432 that are annexed thereto. Thus, as schematically illustrated by double arrows in FIG. 3, the positions of these lenses can be moved in the direction of the optical axis for positional adjustment. As will be described in greater detail hereinafter, the positional adjustment using these position adjustment mechanisms 431, 432 is for suppressing the resonant bandwidth and not for scanning.

In other words, the scan control section (not illustrated) for angle scanning drives only the rotary mechanism 420 to operate for angle scanning but never drives the position adjustment mechanisms 431, 432 during an operation of angle scanning. The scan control section may be an independent unit or alternatively it may part of the control device for controlling each of the components of the entire detection apparatus. While the concave mirror 408 may be annexed to the position adjustment mechanism 441, the position adjustment mechanism 441 is never driven during an operation of angle scanning.

When the technique of polarization multiplexing detection is employed, each of the polarization components may be detected by means of the half-wave plate 414, the polarization beam splitter 415 and two detectors 413a and 413b. When the technique of synchronization detection is employed, a single polarization component may be subjected to intensity modulation by means of the modulator 402 or two polarization components that are orthogonal relative to each other may be subjected to intensity modulation by means of different frequencies. Light emitted from the beam splitter 404 may be detected by way of an aperture 409 in order to remove any stray light component. The light loss of the system can be minimized by replacing the beam splitter 404 with a Faraday rotator 410 and a polarization beam splitter 411. However, with such an arrangement, a half-wave plate 412 needs to be inserted between the Faraday rotator 410 and the hemispherical prism 406 in order to adjust the incident polarization.

A drive mechanism may be provided in the direction running in parallel with the optic axial plane of the concave lens 408 in order to accommodate the change in the angle of emergence. However, the number of operating mechanisms can be reduced by one by making the center of curvature of the concave mirror 408 and the center of the hemispherical prism 406 agree with each other so that reflected light may return in the original direction regardless of the angle of emergence. With the known technique, however, the focal plane of incident light and that of feedback light cannot substantially be aligned.

In the detection apparatus of double path arrangement illustrated in FIG. 3, two reflections of the beam of light moving forward and backward contribute to the detected reflectance.

$$R(\theta)=(\int_{-\infty}^{\infty}R'(\theta-\theta')S_f(\theta')d\theta')(\int_{-\infty}^{\infty}R'(\theta-\theta')S_r(\theta')d\theta') \quad (3)$$

The subscripts f and r in the above formula indicate forward path and backward path respectively. In other words, the product of multiplication of the ATR spectrum on the forward path and the ATR spectrum on the way backward path is the contribution to the detected reflectance so that $S(\theta)$ is required to be sufficiently small in each of the paths. For this reason, the resonance curve of the known technique tends to spread widely.

The angular spectrum on the metal film 407a can be approximately given by tracing the propagating Gaussian beam. If the Gaussian type intensity distribution is assumed to be I(r), it can be characterized by the radius of curvature R and the width w of the beam at a predetermined position. Then, the angle of the wavefront and the optical axis at a position separated from the optical axis by distance r is expressed by the formula illustrated below.

$$\theta=\sin^{-1}(r/R)$$

Thus, $S(\theta)$ can be expressed as $S(\theta)=I(R \sin \theta)$, using an parameter expression of I(r). Therefore, the actual ATR spectrum can be determined by computing the propagation of the Gaussian beam, determining S(θ) from w and R on the sample surface and using the formula (3) for approximately computation. From the above, it will be seen that the beam diameter w needs to be small and the radius of curvature R needs to be large on the sample surface for the purpose of suppressing the wide spread of the ATR spectrum.

It is known from FIG. 2 that the spread of the resonance signal can be substantially suppressed when $\theta_{FWHM} < 0.1°$. Therefore, an arrangement that meets the above requirement can be computationally determined in a manner as illustrated below. Assuming the use of a single mode fiber light source of wavelength of 800 nm, parameters including the position x of the collimator lens 401 from the light emitting end of the fiber of the light source 400 and the distance y between the converging lens 405 and the hemispherical prism 406 will be employed.

When $$C = \sqrt{(\theta^f_{FWHM})^2 + (\theta^r_{FWHM})^2}$$

is defined as evaluation function, the region that can sufficiently reduce the width of the actual ATR spectrum given by the formula (3) can be identified by minimizing the value of the evaluation function.

Figure 4:
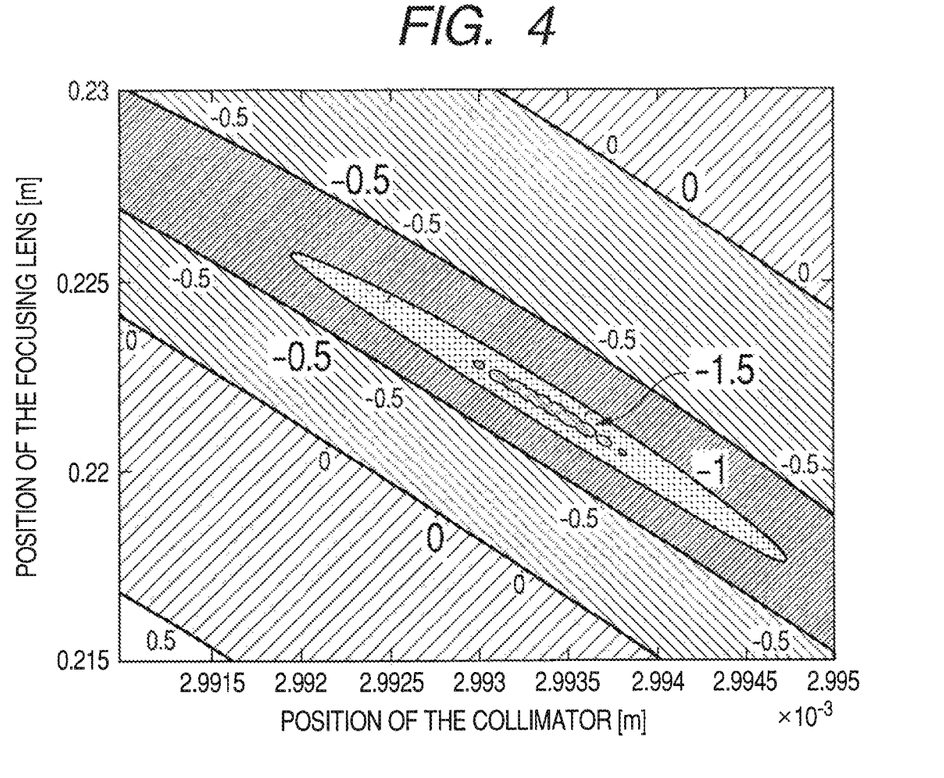
FIG. 4 is a illustration indicating how the evaluation function C changes when the position x of the collimator lens from the light emitting end of the fiber and the distance y between the converging lens and the hemispherical prism are made to vary.

FIG. 4 illustrates an example of evaluation function. FIG. 4 illustrates the distribution of the values of log(C), where the horizontal axis and the vertical axis indicate x and y respectively.

From FIG. 4, it is known that there exists a region where C<0.1 (that is, log(C)<−1) holds true. Considering a Gaussian beam that comes back to the collimator lens 401 after being transmitted through a series of optical systems, the ABCD matrix thereof substantially satisfies the self-reproduction condition.

$$|(A+D)/2| \leq 1$$

Additionally, the Gaussian beam is characterized in that the focal point of the beam is located on the sample 407 or its vicinity and the half diameter of the beam changes little at and near the focal point thereof. As a result, the beam diameter is in the order of not more than 100 microns on the sample surface. The influence of spherical aberration is practically negligible if the hemispherical prism 406 has a size of about 1 cm.

With the known ATR apparatus illustrated in FIG. 8, the hemispherical prism 504 is required to have a large size because collimated beam of light is made to enter the hemispherical prism 504.

Figure 5:
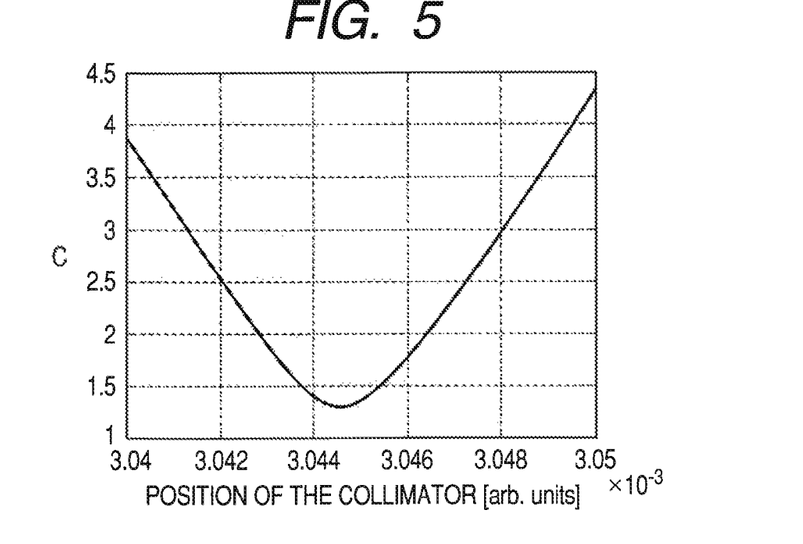
FIG. 5 is a graph illustrating how the evaluation function C, which is similar to that of FIG. 4, changes when the position of the collimator lens is varied with a known technique.

On the other hand, the value of C is not smaller than 1 as illustrated in FIG. 5 if a similar evaluation function is defined for a known system and the position of the collimator lens is shifted.

Note here that only the position of the collimator lens is selected as adjustment parameter in the known system because collimated light is employed without using divergent light. Differently stated, it is safe to say that the known system does not employ any converging lens. Since the value of C is larger than 1, it is clear by seeing FIG. 2 that the resonant bandwidth is inevitably broadened in the known system.

As described above, the detection apparatus of this embodiment as illustrated in FIG. 3 can limit the number of operating mechanisms for scanning to one and suppress any broadening of the resonant bandwidth.

In other words, the beam on the surface of the hemispherical prism 406 through which the beam enters the latter is made sufficiently small by using divergent light as light to be entered into the curved surface prism so that the spherical aberration can be reduced. While the spherical aberration can be reduced by increasing the half diameter of the hemispherical prism 406, the half diameter of the hemispherical prism 406 is minimized by using a converging lens 405 so that the entire apparatus is prevented from becoming large and the spherical aberration can be reduced at the same time.

The position of the collimator lens 401 and that of the converging lens 405 can be adjusted by using the position adjustment mechanisms 431 and 432 respectively. Thus, as a result, the radius of curvature of the beam on the reflecting surface of the hemispherical prism can be optimized both on the way moving forward and on the way moving backward. Then, the peak that illustrates the angle dependency of the optical signal relative to the change in the test sample 407c is prevented from being broadened.

Thus, this embodiment can realize an optical signal monitor that inherits the advantage of a small and simple configuration of the heretofore known double path arrangement and, at the same time, illustrates a degree of precision that is higher than ever.

EXAMPLE 1

A converging lens 405 of f=150 mm, a hemispherical prism of R=5 mm and a concave mirror of R=50 mm are employed for a detection apparatus as illustrated in FIG. 3 to observe an ATR signal. A polarization-holding single-mode optical fiber-coupled type LD light source is used and the diameter of the collimated beam is about 1 mm or less on the converging lens.

The position of the concave mirror 408 is defined so that the position of the returning beam of light may not be shifted by angle scanning and the position of the converging lens 405 is adjusted so as to reduce the resonant bandwidth, while observing the ATR signal. As a result, the maximum value of inclination of the sloped part in the formula (1) can be increased to about ⅓ of the value given from the profile of FIG. 1. Additionally, the value of the sloped part in the formula (1) can be made substantially equal to the ideal maximum value by aligning the collimator lens 401 to the degree of positional precision of the order of 100 nm (that can achieve desired position x). When the positional precision requirement needs to be alleviated, a substitute of the adjustment mechanism of parameter x can be realized by inserting a telescope between the collimator lens 401 and the polarizer 402 and adjusting the magnification.

After making sure that the resonant bandwidth is minimized by angle scanning, the angle of incidence to the sample 407 is fixed to angle θ that provides the maximum value of the sloped part in the formula (1) for a detecting operation.

As a result, the dynamics generated on the test sample 407c can be traced with a high degree of sensitivity as changes in the optical signal detected by the detector 413. When polarization multiplexing detection is conducted, the half-wave plate 403 is driven to rotate such that the powers of the two light waves produced by the polarization beam splitter 415 are balanced with each other.

The polarization beam splitter 415 is aligned with the axis of polarization of the light emitting end of the fiber. Then, signal can be detected with an improved sensitivity by modulating the intensity by means of the modulator 402 and also by synchronous detection. It may be needless to say that the light source 400 may be directly modulated instead of using the modulator 402.

EXAMPLE 2

In this example, a cylindrical prism (hemicylindrical prism) is employed as curved surface prism.

Figure 6:
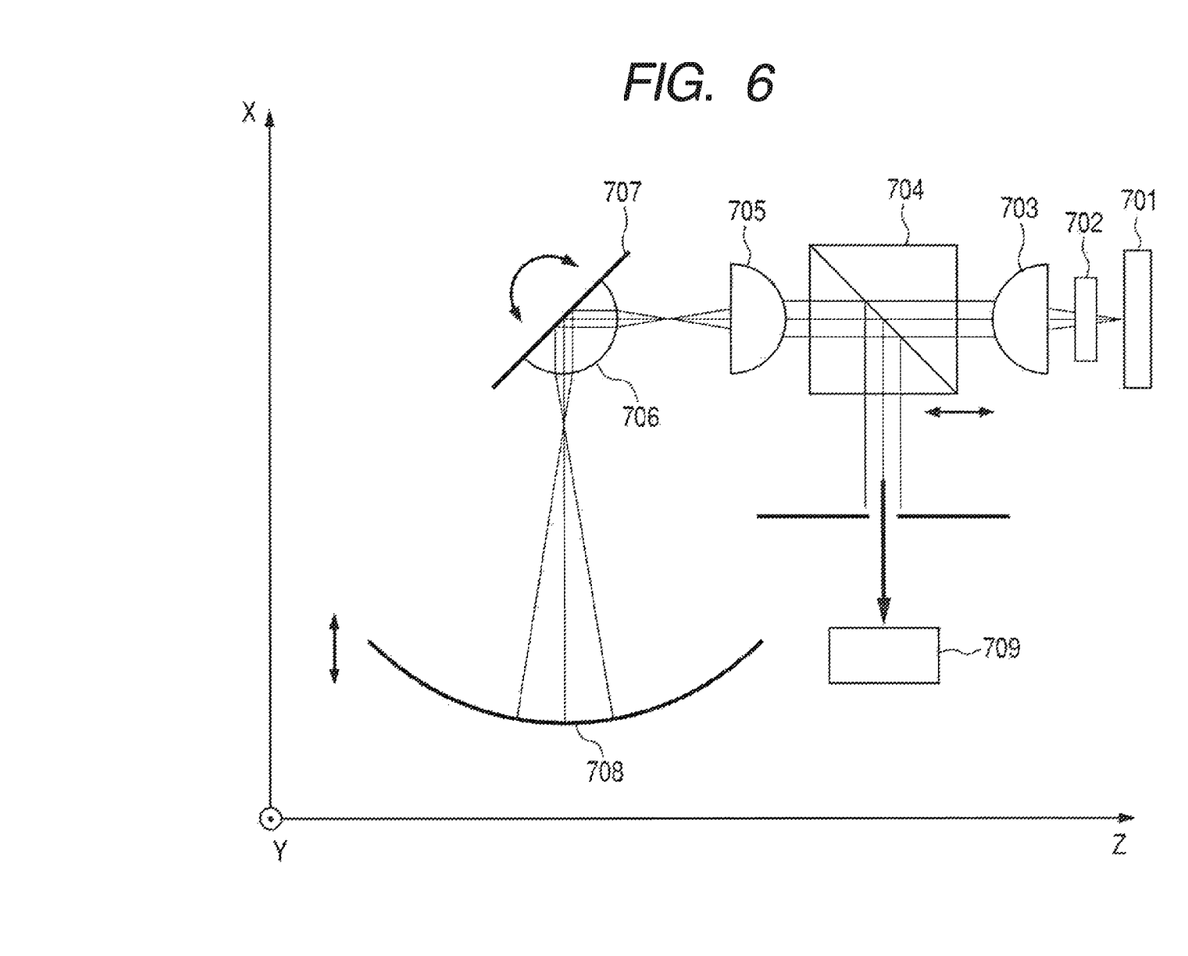
FIG. 6 is a schematic illustration of another embodiment of detection apparatus according to the present invention.

In the detection apparatus illustrated in FIG. 6, light emitted from the laser diode 701 that operates as light source illustrates different divergence angle values on the axes orthogonal to each other within the beam. Thus, the beam profile is of an elliptic type and the beam is collimated by means of cylindrical lenses 702 and 703 on the x- and y-axes independently.

After passing through the beam splitter 704, the beam is irradiated on the sample 707. If the direction illustrating a large divergence angle is that of the x-axis, a focused beam is generated by means of the cylindrical lens 705 that is arranged perpendicularly relative to the x-axis and focused on the focal plane of the cylindrical prism 706.

Thus, the beam passes through the cylindrical prism in a state of being collimated in the y-z plane, whereas the beam is collimated in the cylindrical prism, irradiated on the sample and then converged again outside the cylindrical prism in the x-z plane.

The beam is reflected by the reflecting mirror 708 and follows the route similar to that of the first path before the beam is received by the photo-detector 709 in the x-z plane.

On the other hand, the beam that is collimated all the way is irradiated onto the sample in the y-z plane. The control of the beam depends on the precision of the distance between the cylindrical collimator lens 702 and the laser diode 701 and can be adjusted independently from other parameters.

Arrangements that are required for synchronous detection and polarization multiplexing detection are similar to those described above for Example 1 (FIG. 5). Thus, the anisotropy of beam profile can be utilized advantageously to realize a compact and high performance SPR sensor when the beam profile is elliptic by aligning the beam with the axis of the cylindrical prism as described above in this example.

EXAMPLE 3

Figure 7:
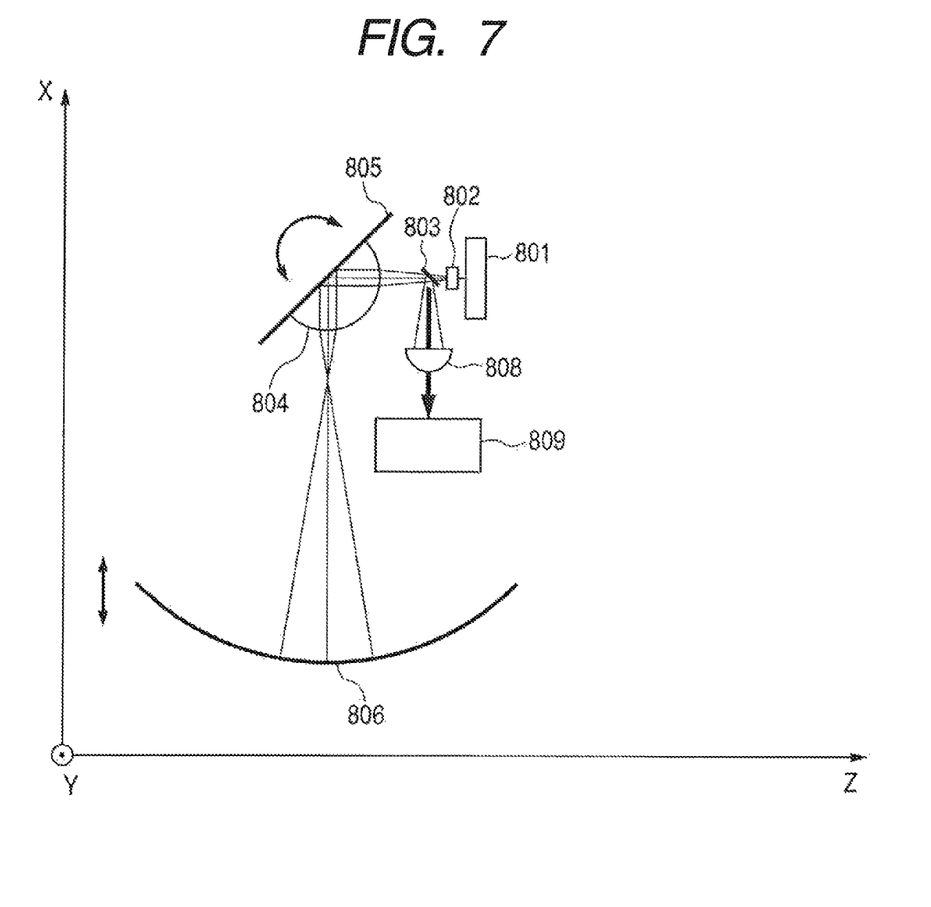
FIG. 7 is a schematic illustration of still another embodiment of detection apparatus according to the present invention.

FIG. 7 illustrates an apparatus having a compact configuration. In the apparatus of FIG. 7, a converging lens is arranged in front of a photo-detector to reduce the number of components necessary for collimation of light emitted from the light source. With the apparatus of FIG. 7, the light emitted from laser diode 801 is collimated by a cylindrical lens 802 in the y-z plane only in one direction. The light is then made to enter a cylindrical prism 804 by way of a beam splitter 803. The focal point of the cylindrical prism 804 is made to agree with the emitter position of the laser diode 801 so that the divergent light is collimated by the cylindrical prism 804 and irradiated onto sample 805. The reflected light is then reflected by cylindrical mirror 806 as in the case of FIG. 6 and directed to the detection stage. With the above-described arrangement, the detected light can be taken out as divergent beam of light so that an effective beam can be re-converged to a photo-detector 809 by means of a converging lens 808 to realize a highly efficient detection. The beam splitter 803 preferably illustrates a weak angle dependency.

While a laser diode is employed in this example, it may be clear that a more simple configuration can be realized when a light source for emitting a collimated beam of light is used.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent No. 2007-180899, filed Jul. 10, 2007, which is hereby incorporated by reference herein in its entirety.

What is claimed is:

1. A detection apparatus comprising a light source for emitting light, a curved surface prism having a curved surface and a plane surface, a metal film placed on the plane surface to be held adjacently to a test sample, and a reflecting member for reflecting light, wherein the light source, the curved surface prism, the metal film and the reflecting member are arranged such that light emitted by the light source enters the prism through the curved surface and is reflected by the metal film, then by the reflecting member, and again by the metal film, wherein the apparatus is adapted to detect an optical change in the test sample by means of surface plasmon generated on the metal film, and wherein divergent light is made to enter the curved surface of the prism to collimate the incident light by means of the curved surface.

2. The apparatus according to claim 1, wherein the reflecting member is separated from the curved surface prism.

3. The apparatus according to claim 1, further comprising a rotary mechanism for driving the curved surface prism to rotate.

4. The apparatus according to claim 1, wherein the divergent light is focused immediately before entering the curved surface prism.

5. The apparatus according to claim 1, wherein the divergent light is obtained by causing light emitted from the light source to pass through a converging lens.

6. The apparatus according to claim 5, wherein the light is obtained by causing collimated light to enter the converging lens.

7. The apparatus according to claim 5, wherein the reflected light is made to enter the detector after passing through the converging lens.

8. The apparatus according to claim 6, wherein the collimated light is obtained by causing emitted light to pass through a collimator lens.

9. The apparatus according to claim 8, further comprising a position adjustment mechanism of the collimator lens and a position adjustment mechanism of the converging lens.

10. The apparatus according to claim 9, wherein the collimator lens and the converging lens are movable by means of the respective position adjustment mechanisms so that the incident light has an angular spectrum showing a half bandwidth not greater than 1/10 of the half bandwidth of the resonance spectrum at the position of the light converging point on the metal film both on the way moving forward from the light source to the metal film and on the way moving backward from the reflecting mirror to the metal film.

11. The apparatus according to claim 8, wherein, when a Gaussian beam that comes back to the collimator lens after being transmitted from the starting point of the collimator lens through a series of optical systems including the converging lens, the curved surface prism, the metal film and the reflecting member is considered, an ABCD matrix thereof substantially satisfies the requirement of the formula illustrated below $|(A+D)/2| \leq 1.$ 12. The apparatus according to claim 1, wherein the curved surface prism is a hemispherical prism.

13. The apparatus according to claim 1, wherein the curved surface prism is a hemicylindrical prism.

14. A method of detecting an optical change in a test sample by means of surface plasmon generated on a metal film comprising:

arranging a light source for emitting light, a curved surface prism having a curved surface and a plane surface, a metal film placed on the plane surface of the prism, and a reflecting member for reflecting light such that light emitted by the light source enters the prism through the curved surface and is reflected by the metal film, then by the reflecting member, and again by the metal film;

bringing the test sample into contact with the metal film;

having the light source emit light and making the light enter the prism through the curved surface as divergent light; and making the light reflected by the metal film, by the reflecting member and again by the metal film to enter a detector to detect a change in resonance condition of surface plasmon generated on the metal film in response to an optical change in the test sample.

15. The method according to claim 14, wherein the test sample contains an antigen and the metal film holds an antibody, whereby the method is adapted to detect the change in resonance condition due to a specific reaction of the antibody and the antigen.

16. The method according to claim 14, wherein the optical change is a change in permittivity of a surface of the metal film.

* * * * *